United States Patent [19]
Scheyer

[11] Patent Number: 5,758,675
[45] Date of Patent: Jun. 2, 1998

[54] DENTAL APPLIANCE WASHER

[76] Inventor: Warner F. Scheyer, 1101 N. Northlake Way, Suite #6, Seattle, Wash. 98103

[21] Appl. No.: 587,740

[22] Filed: Jan. 19, 1996

[51] Int. Cl.$^6$ ........................................ B08B 3/02
[52] U.S. Cl. ..................... 134/148; 134/153; 134/147; 134/201
[58] Field of Search ..................... 134/153, 148, 134/139, 130, 902, 147, 901, 201

[56] References Cited

U.S. PATENT DOCUMENTS

| | | | |
|---|---|---|---|
| 2,501,887 | 3/1950 | Cress | 134/148 |
| 2,543,993 | 3/1951 | Stanitz et al. | 134/139 |
| 3,452,763 | 7/1969 | Ballard | 134/139 |
| 4,133,340 | 1/1979 | Ballard | 134/139 |
| 5,492,137 | 2/1996 | Giblin et al. | 134/153 |
| 5,562,114 | 10/1996 | St. Martin | 134/153 |

FOREIGN PATENT DOCUMENTS 995101  8/1976  Canada ............................. 134/139

*Primary Examiner*—Frankie L. Stinson
*Attorney, Agent, or Firm*—Richardson & Folise

[57] ABSTRACT

A washing device for removable dental protheses and other removable dental appliances which includes a base and a removable washing unit mountable on the base. The base has a housing on which the washing unit may be seated, a drive shaft vertically oriented in the housing, and an electric motor for rotating the drive shaft. The washing unit contains a pump adapted to be driven by the drive shaft, a filter assembly, and a fluid reservoir. A denture basket is centrally mounted for free rotation about a vertical axis within the washing unit. Spray nozzles are positioned in the reservoir wall and directed off-center toward the denture basket, causing the basket to rotate as the denture is being cleaned.

12 Claims, 7 Drawing Sheets

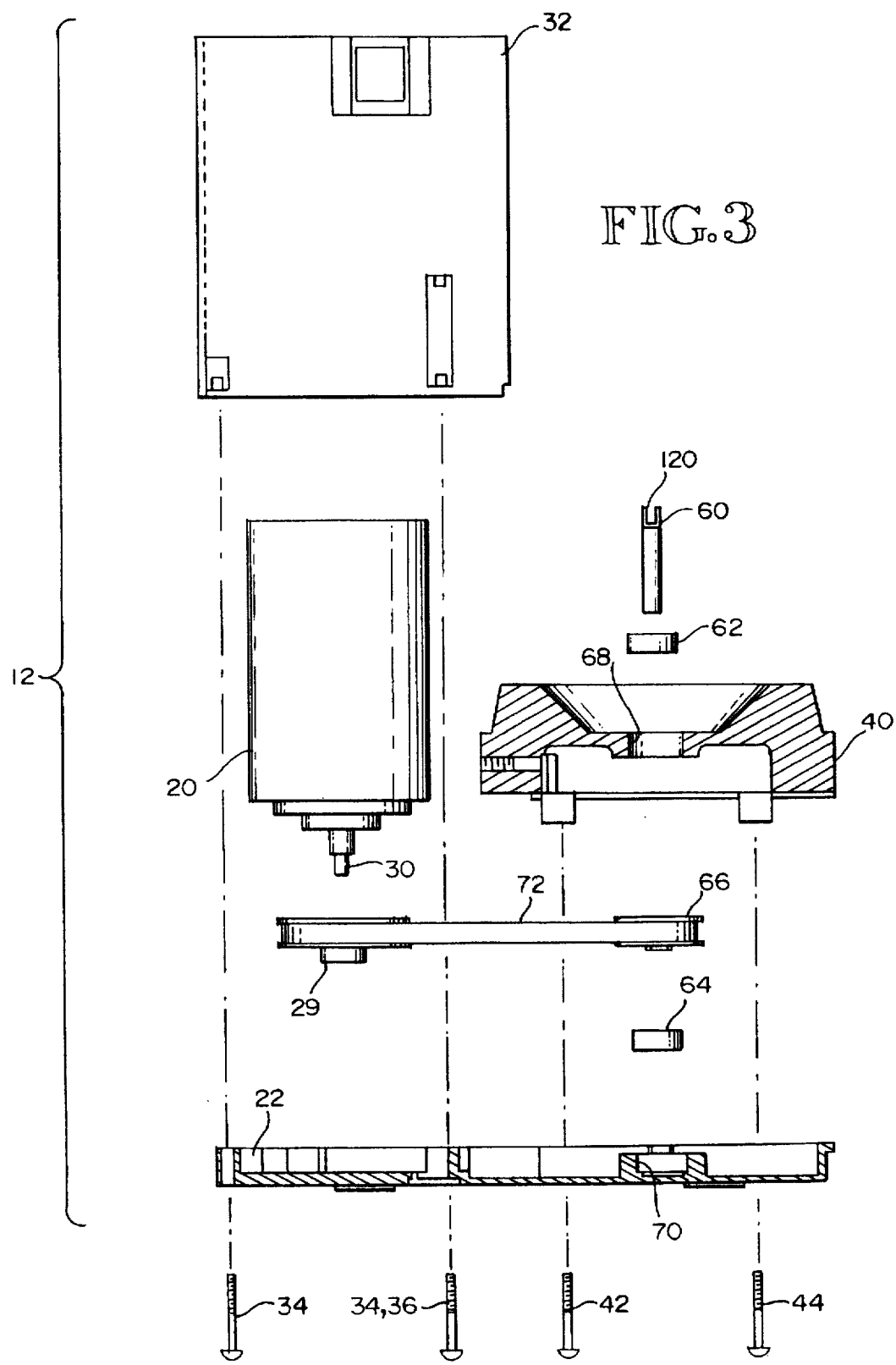

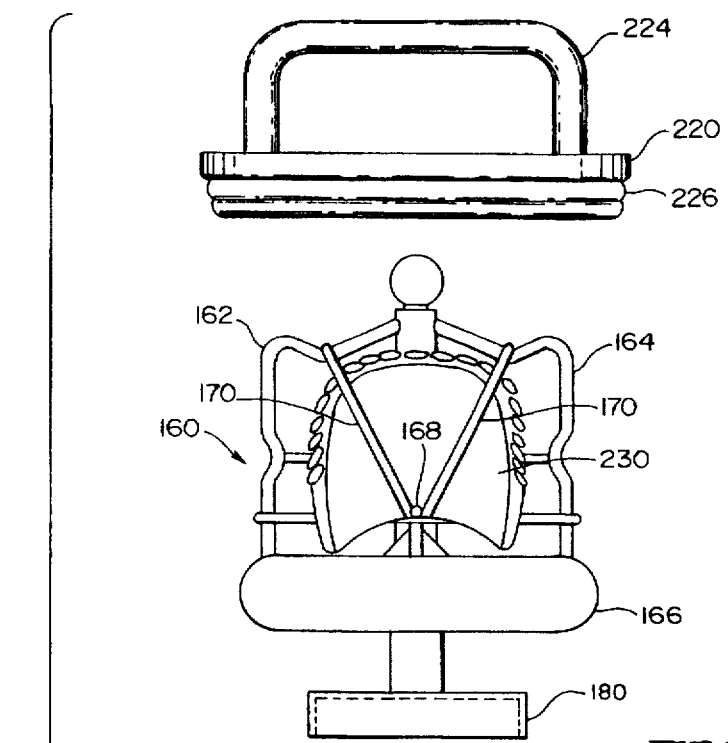
FIG. 4B
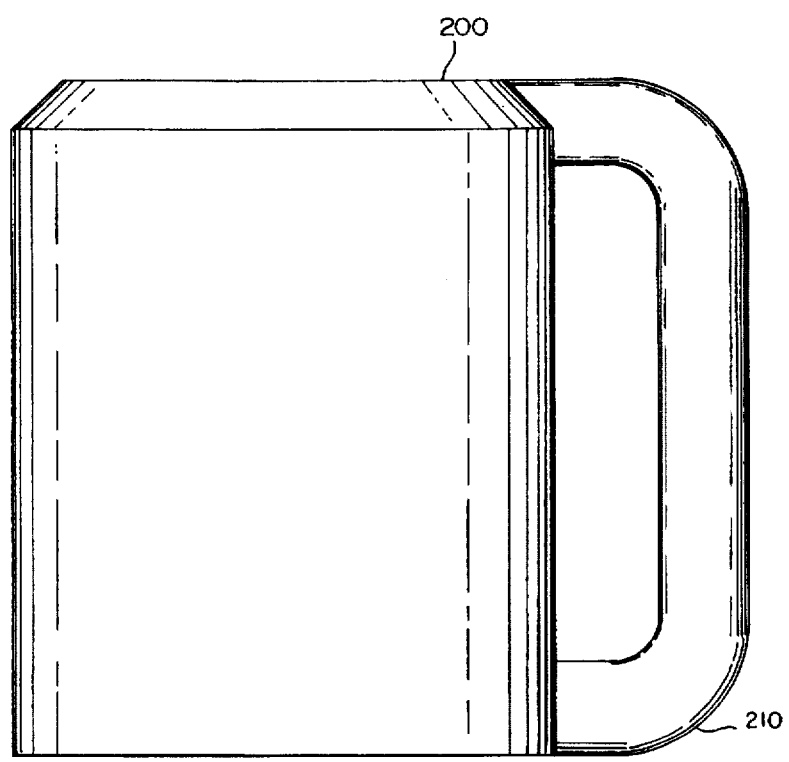

DENTAL APPLIANCE WASHER

BACKGROUND OF THE INVENTION

This invention generally relates to dental appliances and more particularly to a washer for removable dental prothesis and other removable dental appliances.

Removable dental protheses (dentures) and other oral dental appliances require regular and frequent cleaning. Traditionally those devices have been cleaned by soaking them in an antibacterial detergent solution and/or brushing them. Cleanliness is necessary not only for aesthetics but to secure proper fit, eliminate obnoxious odors, and to prevent denture related lesions and bacterial growth.

However, cleaning of dentures by hand is undesirable for a number of reasons. First, it requires handling of the denture by the user or others which increases the risk of contamination. It also increases the possibility that the denture may be accidentally broken by dropping or by the brushing procedure itself. Also, some dentures include very sharp portions which may cause injury to the user and result in infection. Finally, elderly and disabled users may not have sufficient eye-sight, sense of touch, or coordination to effectively clean or maintain dentures.

Another problem faced by the elderly and disabled is that many are required to maintain dentures in an institutional environment. Under such circumstances the possibility of cross contamination is inherently increased, particularly if dentures belonging to a number of users are cleaned together.

Accordingly it is an object of this invention to provide for a washing device for dentures which is highly effective and which eliminates any need for the user to handle the appliance during the cleaning process.

Another object of this invention to provide for such denture washing device particularly suited for use in an institutional environment which will reduce the possibility of cross contamination and provide individualized cleaning units for users.

It is yet another object of this invention to provide for a more efficient denture washing device having a drive unit and an easily removable washing unit, permitting a number of individualized washing units to be used with a single drive unit.

Another object of this invention is to provide for such a cleaning device which is relatively simple to load, operate, and maintain.

A further object of this invention to provide for such a washing device in which dentures can be stored and maintained in a sanitized environment after cleaning.

SUMMARY OF THE INVENTION

This invention can be broadly summarized as providing for a dental appliance washer having a drive unit including a power means and a washing unit removably mountable on the drive unit. The washing unit includes a reservoir, a pump connected to the power means and a dental appliance basket mounted in the reservoir for free rotation about a vertical axis. The basket includes a means for retaining a dental appliance. The washing unit also includes at least one spray nozzle disposed in the reservoir and connected to the pump.

In accordance with the more detailed aspects of the invention the pump is disposed within the base of the reservoir and the pump is positioned within the inner wall of the reservoir. Yet more detailed aspects of the invention include a plurality of vertically spaced nozzles within the reservoir at least one of which is directed horizontally away from the axis of rotation of the basket at a predetermined angle and below the vertical at a second predetermined angle.

In accordance with even more detailed aspects of the invention the drive unit includes a base, an electric motor mounted on the base, a pump drive shaft mounted for rotation in the base and a belt drive interconnecting the motor and the drive shaft.

BRIEF DESCRIPTION OF THE DRAWINGS

FIG. 3 is an exploded side view partially in section of the drive unit of the present invention.

DETAILED DESCRIPTION OF THE PREFERRED EMBODIMENTS

The novel features believed to be characteristic of this invention are set forth in appended claims. The invention itself, however, may be best understood in its various objects and advantages best appreciated by reference to the detailed description below in connection with the accompanying drawings.

Figure 2:
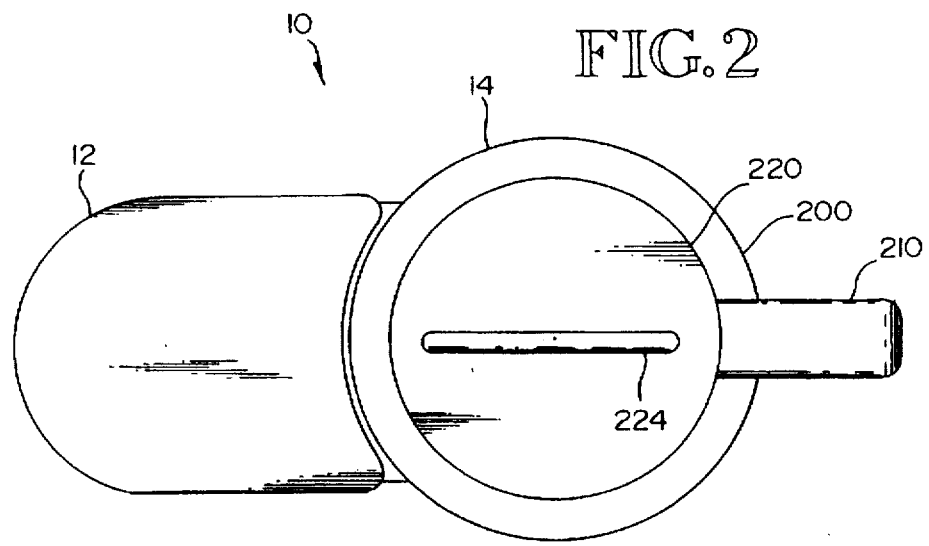
FIG. 2 is a top view of the washer of FIG. 1.
Figure 1:
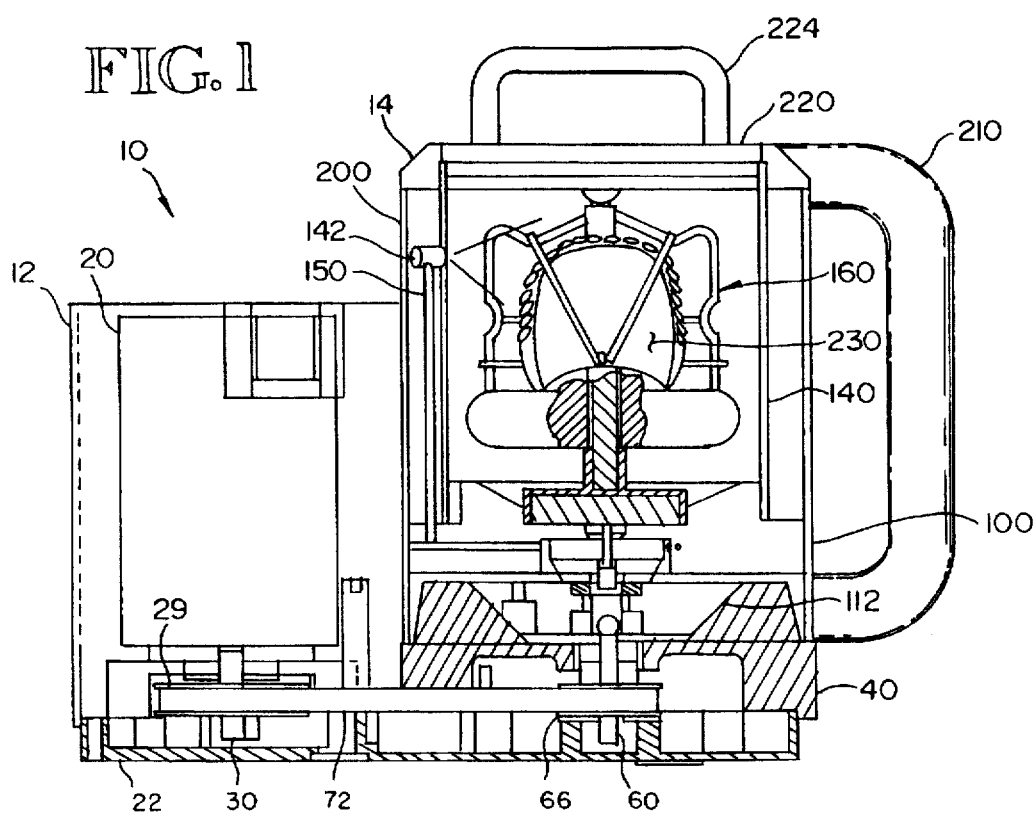
FIG. 1 is a front view partially in section of a dental appliance washer in accordance with the present invention.

FIGS. 1 and 2 illustrate a dental appliance washer constructed in accordance with the teachings of the present invention and generally designated by the number 10. The two principal components of the washer are the drive unit 12 and washer unit 14 which is removably mountable on the drive unit. Referring to the exploded view drawing of the drive unit shown in FIG. 3 it can be seen that it includes motor 20 which is mounted to base 22 by screws 24, 26, and 28 (not shown) which extend upward through the base into the motor housing. Pulley 29 is mounted for rotation with motor shaft 30. Motor cover 32 is positioned over the motor and fastened to the base by screws 32, 34, and 36. Also fastened to the base is housing 40 which is secured with four radially spaced housing screws, of which screws 42 and 44 are typical, which extend upward through the base into the housing as shown. Drive shaft 60 is mounted for vertical rotation on bearings 62 and 64 and pulley 66 is mounted intermediate the bearings for rotation with the drive shaft. Bearing 62 is seated in recess 68 of housing 40 and bearing 64 is seated in recess 40 in base 22. Power is supplied to the drive shaft by motor 20 through pulley 29, drive belt 72 and pulley 66.

Figure 4A:
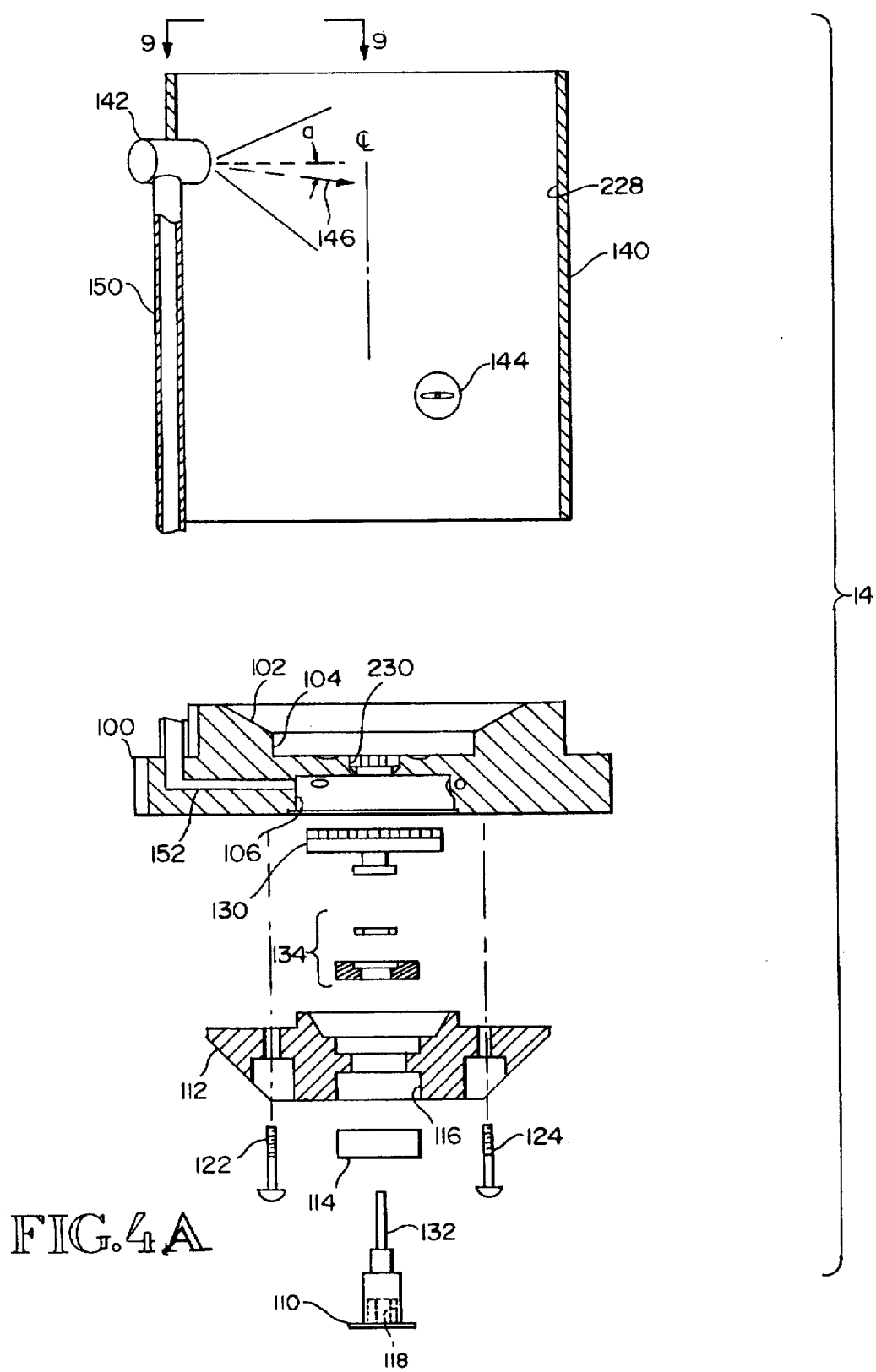
FIG. 4 is an exploded side view partially in section of the washing unit of the present invention.

An important component of this invention is washer unit 14 which is shown in greater detail in exploded view diagram of FIG. 4. Referring to that figure it can be seen that the washing unit includes pump housing 100 which is preferably injection molded from a suitable plastic. Formed in the pump housing are reservoir base 102, filter recess 104, and impeller cavity 106. Pump shaft 110 is mounted for rotation in pump drive cover 112 on bearing 114 which is seated in recess 116 in the pump drive cover. Recess 118 located in the base of the pump shaft is formed to mate with upper end 120 of drive shaft 60. The pump drive cover is mounted to the pump housing by means of six radially spaced pump drive screws of which screws 122 and 124 are typical. Impeller 130, which is mounted on upper end 132 of the pump shaft, is disposed for rotation within impeller cavity 106 and leakage from the cavity along the shaft is prevented by seal assembly 134. Details of the seal assembly are well known and will not be described further.

Figure 9:
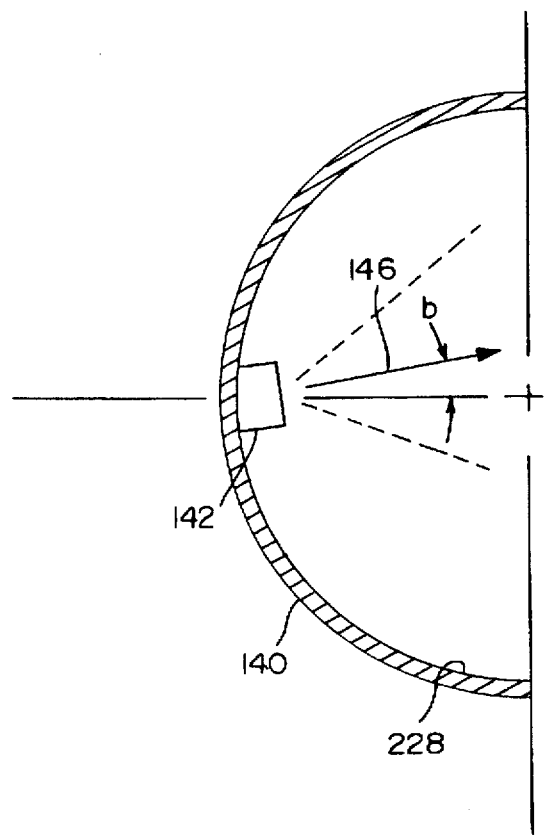
FIG. 9 is a sectional view taken at 9—9 of FIG. 4.

Cylindrical washer reservoir 140, preferably injection molded from a suitable plastic, is sealably mounted on pump housing 100. Three spray nozzles 142, 144 and 146 (not shown), of which nozzle 142 is typical, are mounted in the walls of the reservoir and radially spaced about its vertical centerline at intervals of 120°. The nozzles are also spaced vertically and preferably equally along the center line to provide broad spray coverage. Preferably each of the sprays is directed slightly downward at an angle "a" below horizontal as typically indicated by dashed line 148 representing the spray direction. When viewed from above at least one of the sprays is also directed horizontally slightly to the left or counterclockwise from the reservoir centerline at an angle "b" (see FIG. 9). Communication is provided between spray nozzle 142 and impeller cavity 106 by tube 150 and passage way 152 in the pump housing. Similar tubing segments and passageways (not shown) in the pump housing provide communication between spray nozzles 144 and 146 (not shown).

Figure 5:
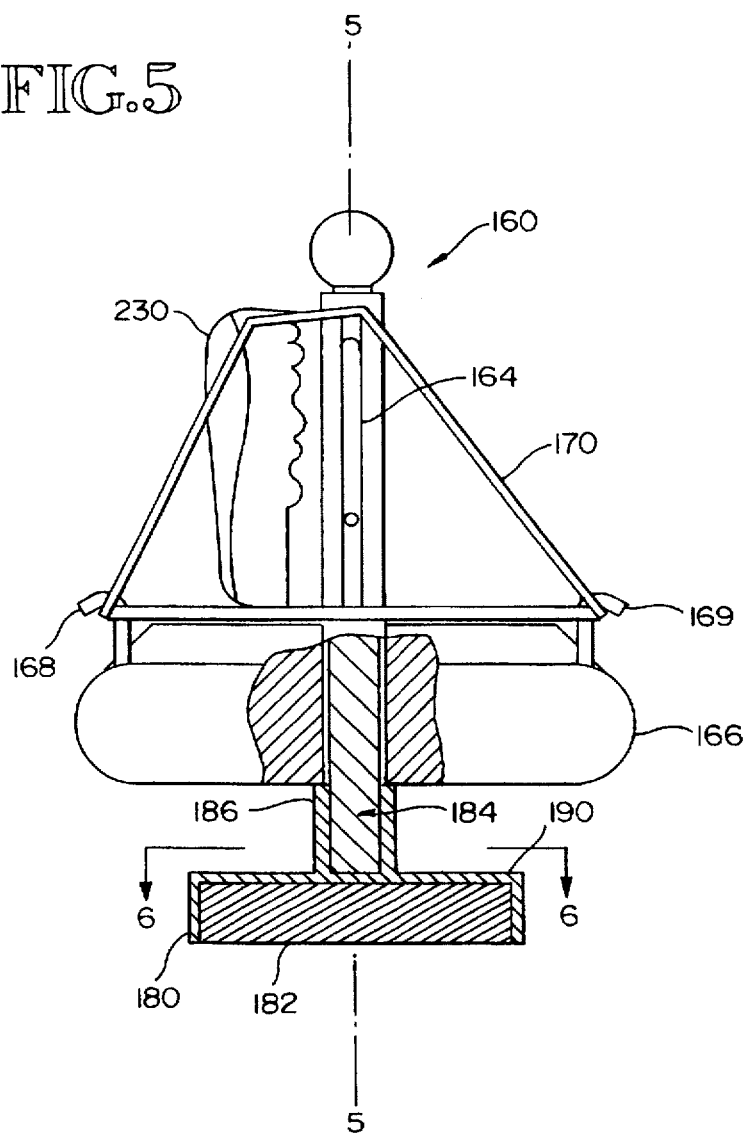
FIG. 5 is a front view partially in section of the denture basket assembly.
Figure 6:
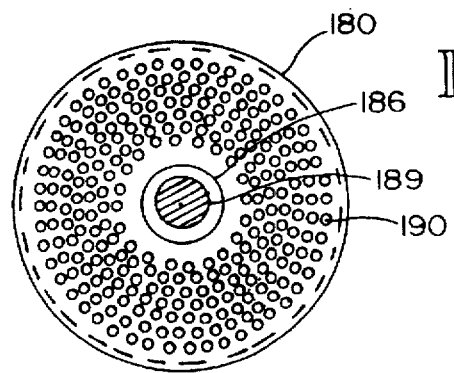
FIG. 6 is a sectional view taken at 6—6 of FIG. 5.

Dentures or other dental appliances to be washed are positioned vertically on denture basket assembly 160 which is shown in detail in FIGS. 4 and 5. The basket assembly includes denture basket 162 formed by vertically oriented frame 164, frame base 166, retaining hooks 168 and 169 and elastic retainer 170. The assembly also includes dispenser filter housing 180 and replaceable porous filter element 182 which is impregnated with an antibacterial/detergent agent. Preferably the filter element is formed of a fine nylon mesh but other suitably materials known to those of ordinary skill may be substituted. Axle 184 is mounted in cylindrical protrusion 186 which extends upward from the filter housing, and denture basket 162 is mounted on the axle for free rotation about vertical axis 5—5 as shown in FIG. 6. Upper surface 190 is perforated by a large number of small diameter holes permitting it to function as a course filter. Outer cup 200 surrounds reservoir 140 and is bonded to circumferential surface 202 of pump housing 100. It includes handle 210 which is enlarged to facilitate handling by elderly and disabled user. Lid 220 including handle 224 and elastomeric seal 226 is adapted to engage inner surface 228 of the reservoir.

Figure 7:
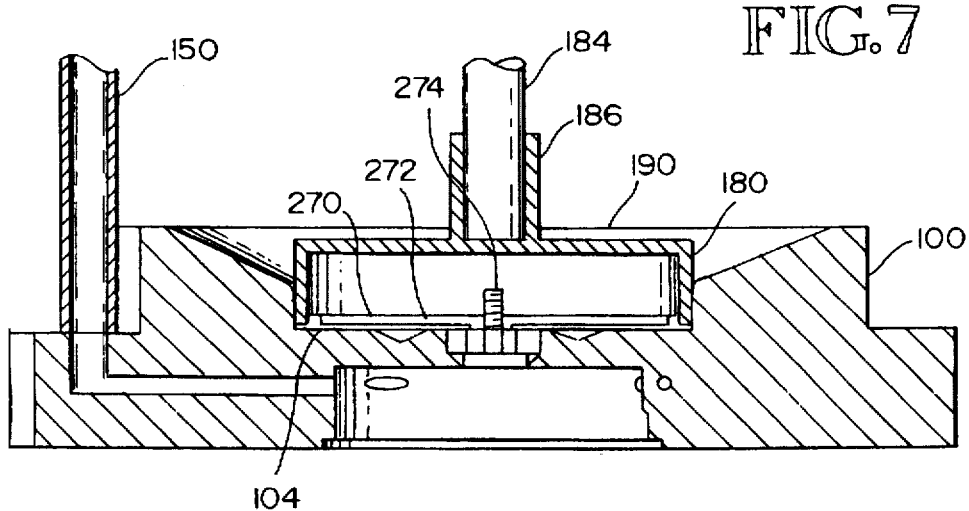
FIG. 7 is a partial sectional view of a second embodiment of the present invention.
Figure 8:
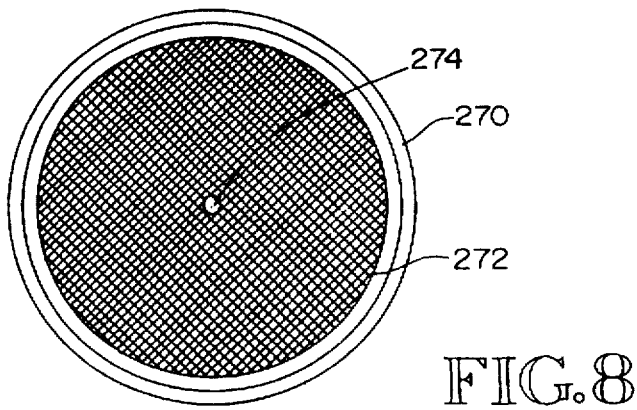
FIG. 8 is a bottom view of the filter housing and screen filter of FIG. 7.

FIGS. 7 and 8 illustrate a second embodiment of the present invention in which filter element 182 has been replaced with a screen filter. As in the first embodiment filter housing 180 includes perforated upper surface 190 which acts to filter relatively long particles from the cleaning fluid. Filter screen 270, which is removably positioned in filter recess 104, includes fine mesh 272 for filtering out much smaller particles. Upwardly extending pin 274 is centrally mounted in the mesh. The filter screen may be cleaned by removing denture basket assembly 160 including housing 180, lifting out the filter by grasping pin 274 and rinsing it. Prior to operation of this embodiment an antibacterial/detergent agent must be added to the water in the reservoir.

In operation a denture such as denture 230 is placed in an upright position on frame base 166 and held securely against frame 164 by elastic retainer 170. Obviously another denture could be secured to the opposing side of the frame in a similar manner. Next an appropriate amount of unheated water is added to the reservoir and a properly cleaned filter element 182 is inserted in filter housing 180. The denture basket assembly is then lowered into the reservoir and the filter housing is positioned in recess 104 of the pump housing. Next, lid 220 is seated in the top of the reservoir and the entire washer unit is positioned on housing 40 with drive shaft 60 inserted in recess 118 of the pump shaft. At this point the washer is ready to operate.

When motor 20 and impeller 130 are energized the fluid in impeller cavity 106 is forced under high pressure through passageway 152 and tube 150 to spray nozzle 142. It is then sprayed under high pressure into the reservoir and toward denture 230. In a similar manner fluid is forced from the impeller cavity to spray nozzles 144 and 146 where it is also directed toward the denture. Because at least one of the nozzles is oriented slightly counterclockwise from the center of the reservoir it produces and off-center force on the denture basket assembly and denture, causing them to rotate continuously about axis 5—5. Obviously, the denture basket could be rotated in the opposite direction if desired by orienting the nozzle(s) clockwise from the centerline. The speed of rotation can be controlled by the extent to which the sprays are directed off-center, the mass flow rate of the sprays, and the friction between the denture basket assembly and axle 184. After leaving the spray nozzles the fluid will flow downward in the reservoir into reservoir base 102 it will continue downward through upper surface 190 of the filter housing which will filter out larger particles from the fluid. It will then continue downward through filter element 182 through pump inlet 230 and finally into impeller cavity 106. As the fluid flows through the filter element additional detergent in the element will continually pass in the solution in the fluid. Preferably a complete cleaning cycle will last approximately one to two minutes. Following cleaning the denture may be hygienically stored in the reservoir if lid 220 is left in position after cleaning is completed.

Thus it can be seen that the present invention provides for an improved dental appliance washer which incorporates many novel features and offers significant advantages over the prior art. Although only two embodiments of this invention have been illustrated and described it is to be understood that obvious modifications can be made of it without departing from the true scope and spirit of the invention.

I claim:

1. A dental appliance washer comprising:
   a self contained closed fluid system washer unit removably mountable on the drive unit and including an outer cup, a reservoir base having an upper surface forming a sump for the collection of cleaning fluid, a washer reservoir disposed within and spaced from the outer cup and mounted on the reservoir base, a plurality of spaced nozzles mounted to the washer reservoir and a plurality of tubing segments each disposed between the outer cup and the reservoir base and connecting one of the nozzles to the pump, a pump disposed within the reservoir base beneath the sump, and a filter removably mounted in the sump for filtering cleaning fluid passing into the pump; and,
   a drive unit including power means removably connectable with the pump.

2. The dental appliance washer of claim 1 including a dental appliance basket mounted within the washer reservoir for free rotation about a vertical axis and including means for retaining a dental appliance.

3. The dental appliance washer of claim 2 wherein the means for retaining includes a frame for retaining the appliance in a vertically oriented position.

4. The dental appliance washer of claim 2 wherein the dental appliance basket is mounted to the filter.

5. The dental appliance washer of claim 1 wherein at least one of the nozzles is directed below the horizontal at a predetermined angle "a".

6. The dental appliance washer of claim 1 wherein at least one of the nozzles is directed horizontally away from the axis of rotation of the basket at a predetermined angle "b".

7. The dental appliance washer of claim 1 wherein the power means is an electric motor.

8. The dental appliance washer of claim 1 further including a base and wherein the electric motor is mounted to the base.

9. The dental appliance washer of claim 1 wherein the drive unit includes a pump drive shaft removably connectable to the pump.

10. The dental appliance washer of claim 1 wherein the drive unit includes a motor pulley connected to the power means, a pump drive shaft mounted for rotation in the base and slidably connectable to the pump, a drive pulley connected to the pump drive shaft and a drive belt connecting the pulleys.

11. A dental appliance washer comprising:

a self contained closed fluid system washer unit removably mountable on the drive unit and including an outer cup, a reservoir base having an upper surface forming a sump for the collection of cleaning fluid, a washer reservoir disposed within and spaced from the outer cup and mounted on the reservoir base, a plurality of spaced nozzles mounted to the washer reservoir and a plurality of tubing segments each disposed between the outer cup and the reservoir base and connecting one of the nozzles to the pump, a pump disposed within the reservoir base beneath the sump, and a filter removably mounted in the sump for filtering cleaning fluid passing into the pump, a dental appliance basket mounted to the filter for free rotation about a vertical axis and including means for retaining a dental appliance; and, a drive unit including power means removably connectable with the pump.

12. A dental appliance washer comprising:

a self contained closed fluid system washer unit removably mountable on the drive unit and including an outer cup, a reservoir base having an upper surface forming a sump for the collection of cleaning fluid, a washer reservoir disposed within and spaced from the outer cup and mounted on the reservoir base, a plurality of spaced nozzles mounted to the washer reservoir wherein at least one of the nozzles is directed below the horizontal at a predetermined angle "a" and horizontally away from the axis of rotation of the basket at a predetermined angle "b", a plurality of tubing segments each disposed between the outer cup and the reservoir base and connecting one of the nozzles to the pump, a pump disposed within the reservoir base beneath the sump, and a filter removably mounted in the sump for filtering cleaning fluid passing into the pump, a dental appliance basket mounted to the filter for free rotation about a vertical axis and including means for retaining a dental appliance; and, a drive unit including a base, an electric motor mounted to the base, a motor pulley connected to the electric motor, a pump drive shaft mounted for rotation in the base and slidably connectable to the pump, a drive pulley connected to the pump drive shaft and a drive belt connecting the pulleys.

* * * * *